United States Patent [19]

Chan

[11] 4,395,572
[45] * Jul. 26, 1983

[54] PROCESS FOR PREPARING N-ALKYL-NITROANILINES

[75] Inventor: John K. Chan, Charleston, W. Va.

[73] Assignee: Union Carbide Corporation, Danbury, Conn.

[*] Notice: The portion of the term of this patent subsequent to Sep. 15, 1998, has been disclaimed.

[21] Appl. No.: 255,425

[22] Filed: Apr. 20, 1981

Related U.S. Application Data

[63] Continuation-in-part of Ser. No. 107,537, Dec. 27, 1979, Pat. No. 4,289,907.

[51] Int. Cl.$^3$ ...................... C07C 89/02; C07C 85/06
[52] U.S. Cl. .................................... 564/399; 564/401
[58] Field of Search ........................ 564/399, 315, 401

[56] References Cited

U.S. PATENT DOCUMENTS 3,672,866  6/1972  Damiano .............................. 71/121
3,991,116  11/1976  Damiano ............................ 260/577
4,289,907  9/1981  Chan .................................... 564/399

OTHER PUBLICATIONS

Bunnett et al., "J. Org. Chem.," vol. 33, pp. 2320–2324 (1968).
Morrison & Boyd, "Organic Chemistry," 3rd Edition, pp. 555–559 (1972).
Fierens et al., "Chem. Ab.," vol. 50, Abstract No. 11260(b).

Primary Examiner—John Doll
Attorney, Agent, or Firm—Robert C. Brown; Dale L. Carlson; William R. Moran

[57] ABSTRACT

This invention relates to a process of preparing N-alkyl-nitroanilines selected from the group consisting of N-alkyl-mononitroanilines and N-alkyl-dinitroanilines by the O-alkylation of a nitrophenol to produce the corresponding alkoxy derivative, followed by reaction of the alkoxy derivative with alkylamine to produce the desired N-alkyl-nitroaniline.

7 Claims, No Drawings

PROCESS FOR PREPARING N-ALKYL-NITROANILINES

This application is a continuation-in-part of Ser. No. 107,537, filed Dec. 27, 1979, now U.S. Pat. No. 4,289,907.

FIELD OF THE INVENTION

This invention relates generally to the production of N-alkyl-nitroanilines and, more particularly, to an improved process for the production of N-alkyl-nitroanilines.

BACKGROUND OF THE INVENTION

N-alkyl-nitroaniline compounds are well known in the art. Certain of these compounds have been found to be important selective herbicides. By way of illustration, the use of N-sec-butyl-4-tert-butyl-2,6-dinitroaniline as a selective herbicide is disclosed in U.S. Pat. No. 3,672,866. The 4-tert-butyl-N-sec-butyl-2,6-dinitroaniline compound and its optically active enantiomorphs are disclosed as useful as herbicides in U.S. Pat. No. 3,991,116. The means of producing the N-butyl-nitroaniline compounds given in the above patents involves the nitration of 4-butylphenol, followed by conversion of the resulting 2,6-dinitrophenol into the chloro-derivative and finally reacting the chloro-derivative with a primary amine to produce the N-butyl-nitroaniline.

The above prior art process is a process that involves the production of a significant amount of chlorinated by-product waste. Consequently, there exists a need for a simpler process of producing N-alkyl-nitroanilines that would eliminate the requirement of disposal of chlorinated waste.

OBJECT

It is an object of the present invention to provide a two-step process of producing N-alkyl-nitroanilines that is inexpensive and does not result in the production of chlorinated waste.

Another object of the invention is to provide a process for preparing N-alkyl-nitroanilines in high purity and yields.

These and other objects will become apparent from a reading of the detailed specification.

SUMMARY OF THE INVENTION

According to the present invention, there is provided an improved process for producing N-alkyl-nitroanilines in high purity and yields by the O-alkylation of a nitrophenol to produce the corresponding alkoxy derivative, followed by reaction of the alkoxy derivative with alkylamine to produce the desired N-alkyl-nitroaniline.

The process for producing N-alkyl-nitroaniline in accordance with the present invention comprises the steps of:

(a) reacting a nitrophenol of the formula:

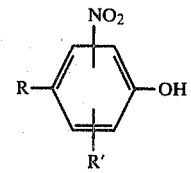

wherein R is $CF_3$ and wherein R' is selected from the group consisting of hydrogen, nitro and $CF_3$, with an alkylating compound selected from the group consisting of alkyl halides, ethylene oxide, propylene oxide, styrene oxide, isobutylene, and mixtures thereof, to form an intermediate product, and (b) reacting said intermediate product with an amine selected from the group consisting of methylamine, ethylamine, isopropylamine, propylamine, butylamine, and mixtures thereof, to produce said N-alkyl-nitroaniline.

The term "intermediate product," as used herein, is used to designate the alkylated or alkoxylated derivative of nitrophenol that is formed in step (a) of the process. As used herein, the term "butylamine" includes sec-butylamine and tert-butylamine, and the term "alkylating compound" encompasses both alkylating and alkoxylating compounds that are presented in the above-specified group of compounds.

DESCRIPTION OF THE PREFERRED EMBODIMENTS

The molar amount of reactants in the process of the present invention can vary over a wide range. Preferably, the nitrophenol is present in an amount of from about 1 to about 50 mole percent, the alkylating compound is present in an amount of from about 50 to about 99 mole percent and the amine is present in an amount of from about 1 to about 99 mole percent, based on the molar amount of the nitrophenol employed.

Although the reactions in accordance with the process of the present invention are preferably conducted in the absence of a solvent, an organic solvent can optionally be employed if desired. Useful solvents include any conventional solvents which do not interfere with the reactions as given in step (a) and step (b) above. Preferred solvents include benzene, toluene, xylene, methanol, acetone, ethyl acetate, methylene chloride and isopropyl ether. The amount of solvent, if used, is not critical.

The reaction temperature can vary widely in the reactions of the invention. For step (a), the preferred temperature range is from about 0° C. to about 300° C.; more preferably, from about 50° C. to about 200° C.; most preferably, from about 100° C. to about 200° C. For step (b), the preferred temperature range is from about −20° C. to about 200° C.; more preferably from about 0° C. to about 100° C.; most preferably, from about 25° C. to about 75° C.

Step (a) of the process of the invention is preferably conducted at autogeneous pressure in an enclosed reactor. If desired, higher pressures of up to 10 atmospheres or higher can be employed.

Step (b) of the process of the invention is preferably conducted in an open reactor at atmospheric pressure. If desired, however, an enclosed reactor can be used at slightly subatmospheric, atmospheric or superatmospheric pressures. If an enclosed reactor is used for step (b), the preferred pressure range is from about 1 to about 5 atmospheres.

The reaction time is not critical and can vary from a few minutes to a day or more depending upon the reaction conditions for each of the steps (steps (a) and (b)). The reaction time for step (a) is preferably between about 2 and about 24 hours. The reaction time for step (b) is preferably between about 10 minutes to about 6 hours.

The process of the present invention will generally provided the N-alkyl-nitroaniline product in high purity and yield. If further purification of product is desired, however, it can be made by conventional means such as recrystallization, liquid-liquid extraction and column chromatography.

The following examples are intended to illustrate, but in no way limit, the present invention.

EXAMPLE I

To a reactor equipped with a reflux condenser was added 24 grams (0.10 mole) of 4tert-butyl-2,6-dinitrophenol, 30 grams (0.21 mole) of methyl iodide, 4 grams (0.11 mole) of potassium carbonate and 150 ml. of anhydrous acetone. The resulting mixture was refluxed under atmospheric pressure for 24 hours. After cooling, the reaction mixture was evaporated under reduced pressure to give a red residue that was then repeatedly extracted with boiling hexane. The combined extracts were filtered hot. Upon cooling, the filtrate yielded 18 grams of a creamy white solid, having a melting point of 94° C. to 96° C. and identified by spectral analysis as 2,6-dinitro-4-tert-butylanisole. The yield of 2,6-dinitro-4-tert-butylanisole was 71 percent based on 2,6-dinitro-4-tert-butyl-phenol reactant.

To a reactor equipped with a reflux condenser was added 2 grams (0.007 mole) of the above-produced 2,6-dinitro-4-tert-butylanisole, and 15 grams of secondary butylamine. The resulting mixture was refluxed at 65° C. for 60 minutes. Upon completion of the reaction, the mixture was evaporated under reduced pressure to remove the excess amine and methanol by-product. The resulting residue, weighing 2.3 grams and having a melting point of 58° to 60° C., was identified by spectral analysis as N-sec-butyl-2,6-dinitro-4-tert-butylaniline. The yield of N-sec-butyl-2,6-dinitro-4-tert-butylaniline was 98 percent based on the 2,6-dinitro-4-tert-butylanisole reactant. The product was found to be essentially pure as indicated by liquid-liquid chromatographic analysis.

EXAMPLE II

To a container was added 20 grams (0.13 mole) of 2,6-dinitro-4-tert-butylphenol, 10 drops of N-methylimidazole, 30 grams of ethylene oxide and 200 ml. of anhydrous toluene. The resulting mixture was transferred to a 600 ml. Parr reactor. The mixture was heated and stirred under pressure to 150° C. and maintained at that temperature for a three to four hour period. After this reaction period, 97 percent of the starting 2,6-dinitro-4-tert-butylphenol was found to be converted into 2-(2,6-dinitro-4-butylphenoxy) ethanol according to liquid-liquid chromatographic analysis. The reaction mixture was then evaporated under reduced pressure to give 23 grams of a dark brown ethoxylated material. The yield of ethoxylated material was almost quantitative based upon 2,6-dinitro-4-tert-butylphenol reactant.

To a reactor was added 18.5 grams (0.065 mole) of the above ethoxylated material and 12 grams of secondary butylamine. The resulting mixture was stirred and heated to between 50° C. and 60° C. for 30 minutes. After cooling, the reaction mixture was poured into ice-water to crystallize the product. The product was recovered by filtration and vacuum-dried to give 18 grams of N-sec-butyl-2,6-dinitro-4-tert-butylaniline having a melting point of 54° C. to 57° C. The yield was 94 percent based on the ethoxylated derivative reactant.

EXAMPLE III

The procedure of Example I was repeated using identical reactants except that 18.4 grams (0.1 mole) of 2,4-dinitrophenol was used instead of the 24 grams of 4-tert-butyl-2,6-dinitrophenol. After reaction, a total of 13 grams of 2,4-dinitroanisole having a melting point of 85° C. to 87° C. was obtained, representing a 66 percent yield based on 2,4-dinitrophenol reactant.

The 2,4-dinitroanisole was converted into N-sec-butyl-2,4-dinitroaniline using secondary butylamine in accordance with the procedure of Example I. The N-sec-butyl-2,4-dinitroaniline having a melting point of 53° C. to 55° C. was obtained in nearly quantitative yield.

What is claimed is:

1. A process for producing N-alkyl-nitroaniline comprising:
   (a) reacting a nitrophenol of the formula:

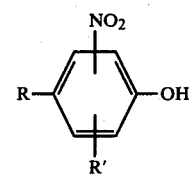

wherein R is $CF_3$, and wherein R' is selected from the group consisting of hydrogen, nitro and $CF_3$, with an alkylating compound selected from the group consisting of ethylene oxide, propylene oxide, styrene oxide, and mixtures thereof, to form an intermediate product and
   (b) reacting said intermediate product with an amine selected from the group consisting of methylamine, ethylamine, isopropylamine, propylamine, butylamine, and mixtures thereof, to produce said N-alkyl-nitroaniline.

2. The process of claim 1 wherein the nitrophenol is present in an amount of from about 1 to about 50 mole percent, the allylating compound is present in an amount of from about 50 to about 99 mole percent and the amine is present in an amount of from about 1 to about 99 mole percent, based on the molar amount of the phenol.

3. The process of claim 1 wherein steps (a) and (b) are carried out in an enclosed reactor and wherein step (a) is carried out at autogeneous pressure and step (b) is carried out at a pressure of from about 1 to about 5 atmospheres.

4. The process of claim 1 wherein step (a) is carried out at autogeneous pressure in an enclosed reactor and step (b) is carried out at atmospheric pressure in an open reactor.

5. The process of claim 1 wherein step (a) is carried out at a temperature of from about 0° C. to about 300°

C. and step (b) is carried out at a temperature of from about −20° C. to about 200° C.

6. The process of claim 5 wherein the temperature for step (a) is from about 100° C. to about 200° C. and the temperatures from step (b) is from about 25° C. to about 75° C.

7. The process of claim 1 wherein the nitrophenol is 4-tert-butyl-2,6-dinitrophenol and the amine is secondary butylamine.

* * * * *

UNITED STATES PATENT AND TRADEMARK OFFICE
CERTIFICATE OF CORRECTION

PATENT NO. : 4,395,572
DATED : July 26, 1983
INVENTOR(S) : J.K. Chan

It is certified that error appears in the above—identified patent and that said Letters Patent is hereby corrected as shown below:

Column 4: line 53; delete "allylating",
    insert ---alkylating---.

Signed and Sealed this

Fourth Day of October 1983

[SEAL]

Attest:

GERALD J. MOSSINGHOFF

Attesting Officer    Commissioner of Patents and Trademarks